(12) United States Patent
Jayaraman

(10) Patent No.: US 6,245,102 B1
(45) Date of Patent: *Jun. 12, 2001

(54) STENT, STENT GRAFT AND STENT VALVE

(75) Inventor: Swaminathan Jayaraman, Fremont, CA (US)

(73) Assignee: Iowa-India Investments Company Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/358,207

(22) Filed: Jul. 21, 1999

Related U.S. Application Data

(63) Continuation-in-part of application No. 08/852,240, filed on May 7, 1997, now Pat. No. 5,855,597, and a continuation-in-part of application No. 09/225,273, filed on Jan. 5, 1999, now Pat. No. 6,162,245.

(51) Int. Cl.[7] .................................................. A61F 2/00
(52) U.S. Cl. ......................................... 623/1.15; 623/1.24
(58) Field of Search .................................. 623/1.1, 1.15, 623/1.16, 1.24

(56) References Cited

U.S. PATENT DOCUMENTS

| | | |
|---|---|---|
| 3,671,979 | 6/1972 | Moulopoulos . |
| 4,056,854 | 11/1977 | Boretos et al. . |
| 4,297,749 | 11/1981 | Davis et al. . |
| 5,332,402 | 7/1994 | Teitelbaum . |
| 5,815,904 | 10/1998 | Clubb . |
| 5,855,597 | 1/1999 | Jayaraman . |

*Primary Examiner*—Michael J. Milano
(74) *Attorney, Agent, or Firm*—Larson & Larson, P.A.; James E. Larson

(57) ABSTRACT

A star-shaped stent and replacement valve or replacement graft for use in repairing damaged vascular organs: Two to eight star-shaped members are interconnected into a "chain". Once this "chain" has been created through interconnection of the star-shaped members, a central opening through all of the interconnected star-shaped members receives a graft made of any suitable flexible and biocompatible material. A catheter delivery system is used to deliver the stent with the graft to the desired site. The star-shaped stents are made by using a laser to cut out a plurality of flat star-shaped members with a plurality of outwardly and inwardly directed points. The outwardly directed points are bent so that they face away from a plane defined by the inwardly directed points and then a series of such stents are fastened together in a chain.

26 Claims, 19 Drawing Sheets

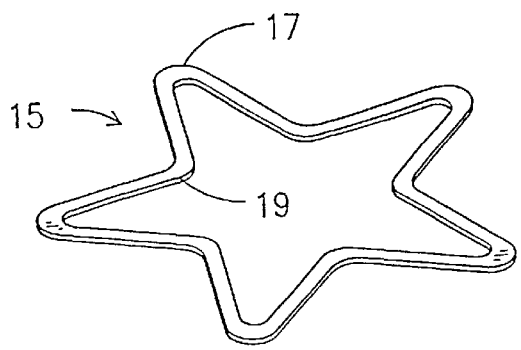
Fig. 3
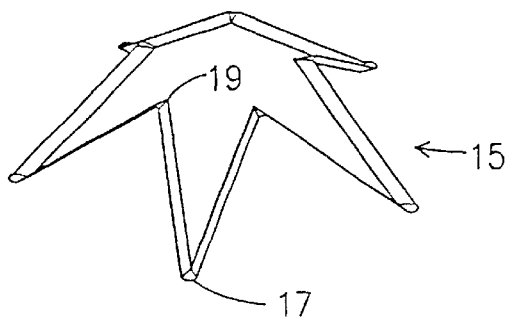
Fig. 4
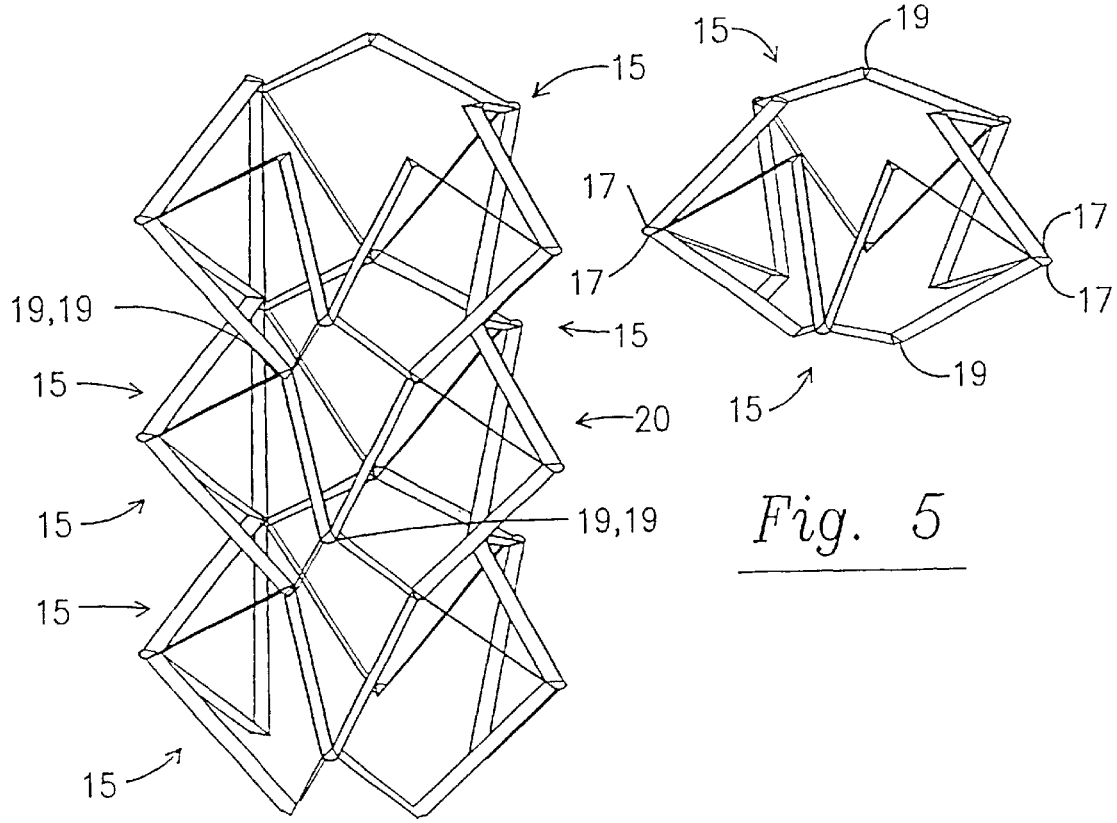
Fig. 6
Fig. 5

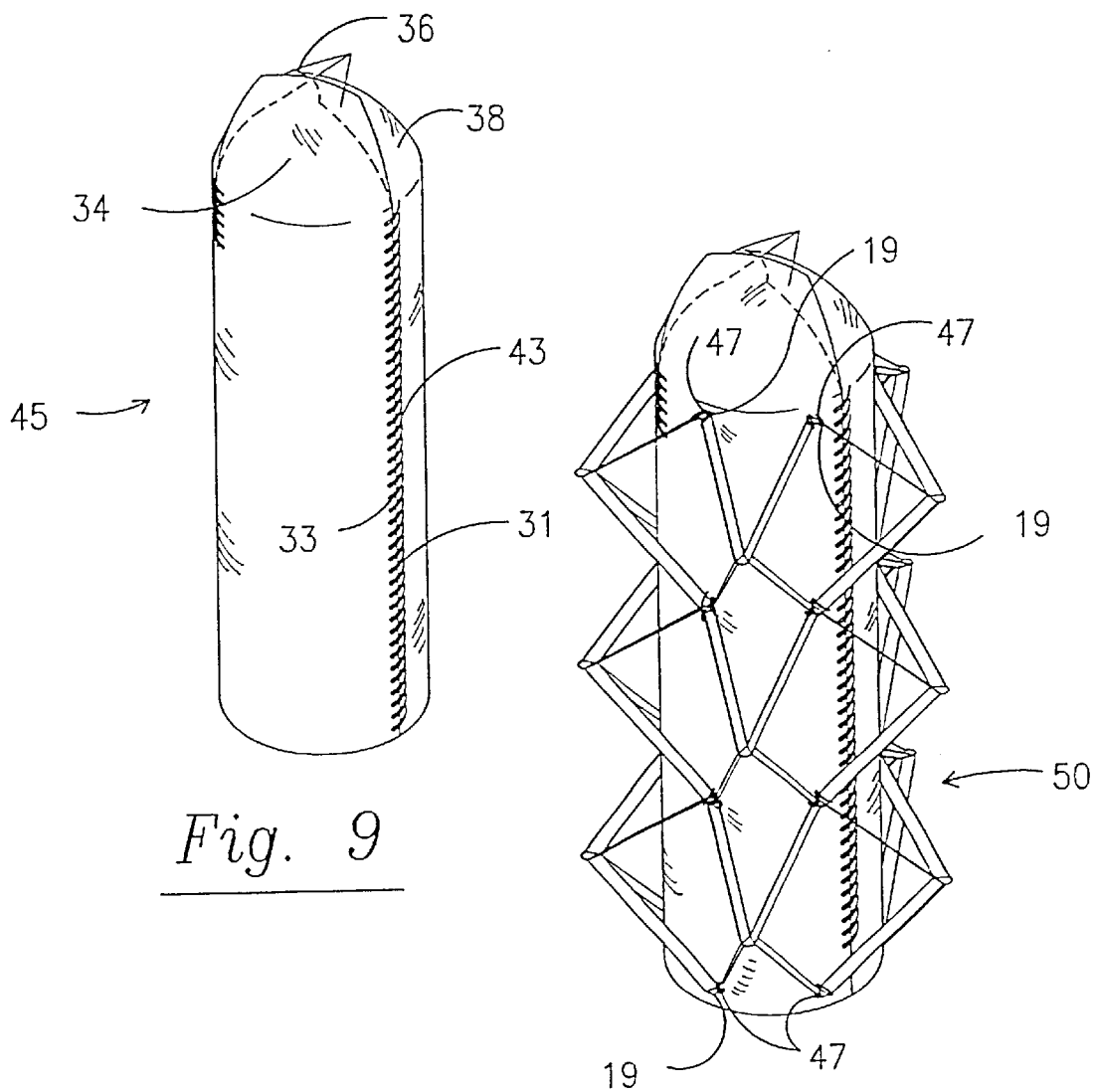

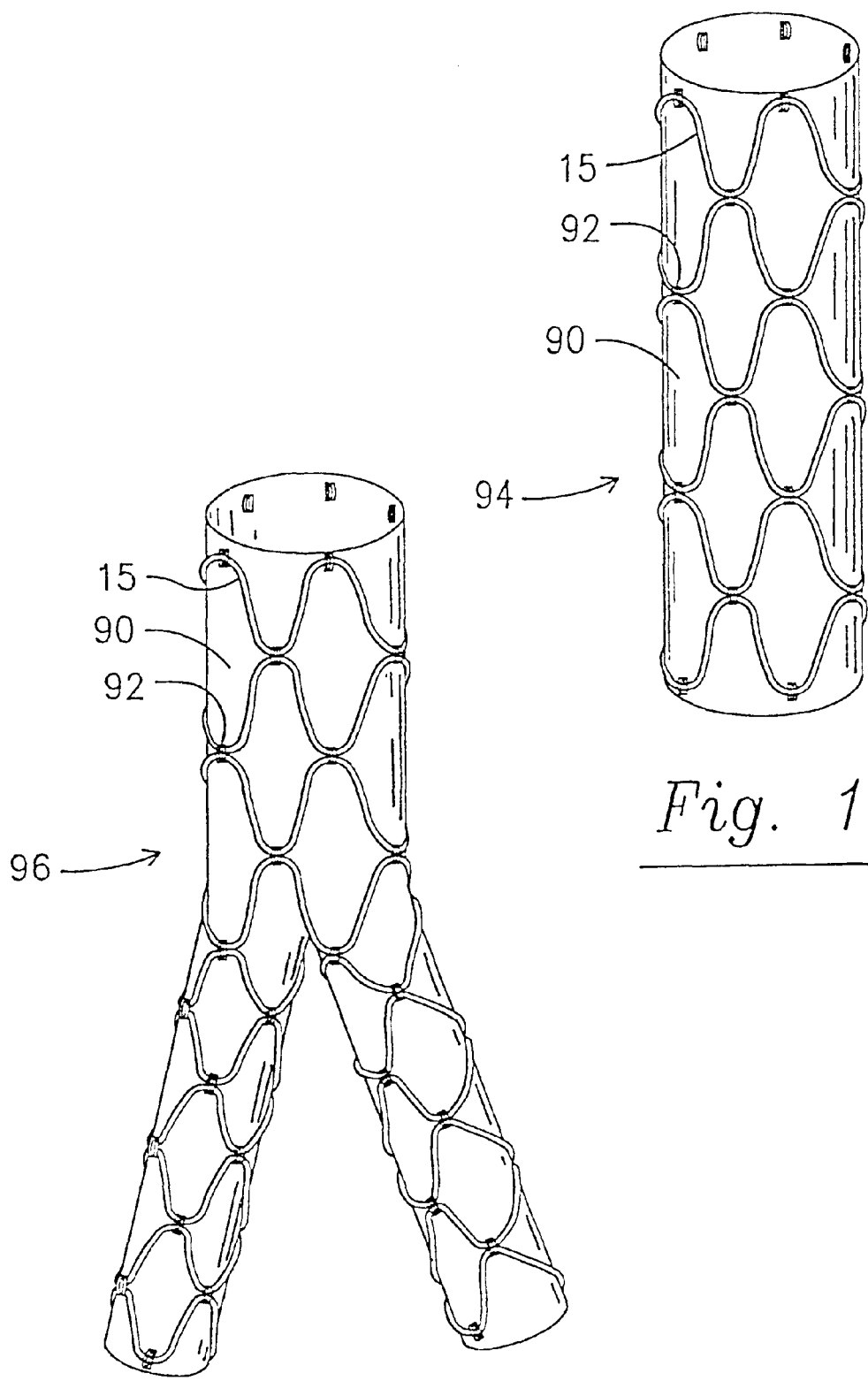

STENT, STENT GRAFT AND STENT VALVE

PRIOR APPLICATION

This application is a continuation-in-part from application Ser. No. 08/852,240, filed May 7, 1997 (now U.S. Pat. No. 5,855,597) and application Ser. No. 09/225,273, filed Jan. 5, 1999, now U.S. Pat. No. 6,162,245.

BACKGROUND OF THE INVENTION

The present invention relates to a star-shaped stent and replacement valve and replacement graft for use in repairing a damaged cardiac valve. In the prior art, stents are known and are employed, usually, to maintain a blood vessel or other body passageway open and free from obstruction.

Applicant is aware of the following United States Patents:

U.S. Pat. No. 3,671,979 to Moulopoulos

U.S. Pat. No. 4,056,854 to Boretos et al.

U.S. Pat. No. 4,297,749 to Davis et al.

U.S. Pat. No. 5,332,402 to Teitelbaum.

These patents relate to repairs to and replacements for cardiac valves. However, none of these references teaches the features and aspects of the present invention.

SUMMARY OF THE INVENTION

The present invention relates to a star-shaped stent and replacement valve for use in repairing a damaged cardiac valve and other vascular bodies. The present invention includes the following interrelated objects, aspects and features:

(1) In a first aspect, the inventive stent is made in a star-shape by cutting it from a flat metal sheet, preferably in the range of 25 to 50 mils in thickness. The metal sheet may be stainless steel, titanium, elgiloy or heat activatable metal such as NITINOL, nickel-titanium alloy. The star shape of the stent includes a thin outline of a star with the center open. Thus, for example, where the star has five outwardly directed points, the same star has five inwardly directed points.

(2) The inventive stent is created by interconnecting from two to eight of these star-shaped members into a "chain".

(3) Once this "chain" has been created through interconnection of the star-shaped members in a manner to be described in greater detail hereinafter, a central opening through all of the interconnected star-shaped members receives a replacement aortic valve tri-cuspid or other vascular graft made of any suitable flexible and bio-compatible material. A catheter delivery system is used to deliver the stent with the aortic valve tri-cuspid to the desired site where it is expanded into position. The chain of stents can be sutured outside a knitted, woven or polymeric extruded tube to replace a diseased portion of an artery in various locations, including the heart.

(4) In the preferred embodiment, each star-shaped member has five points. However, if desired, any number of points from two to five may be suitably employed.

Accordingly, it is a first object of the present invention to provide a star-shaped stent and replacement valve for use in repairing a damaged cardiac valve.

It is a further object of the present invention to provide such a device including a stent made of a plurality of interconnected star-shaped members.

It is a still further object of the present invention to provide such a device including a replacement aortic valve tri-cuspid inserted within the star-shaped members and attached thereto.

It is a still further object of the present invention to provide a stent-graft for percutaneous replacement in the body.

These and other objects, aspects and features of the present invention will be better understood from the following detailed description of the preferred embodiment when read in conjunction with the appended drawing figures.

BRIEF DESCRIPTION OF THE DRAWINGS

FIG. 3 shows a star-shaped member that has been cut from the metal sheet as illustrated in FIGS. 1 and 2.

FIG. 4 shows the star-shaped member of FIG. 3 flexed to a position facilitating attachment to another star-shaped member.

FIG. 5 shows two such star-shaped members attached together by their outwardly directed points.

FIG. 6 shows three pairs of star-shaped members such as the pair shown in FIG. 5, interconnected together with adjacent such pairs being connected by their respective star-shaped member inwardly directed points.

FIG. 9 shows the tube of FIG. 8 but with the slitted end thereof folded in three overlapping pieces to form the tri-cuspid.

FIG. 10 shows the device of FIG. 9 inserted within the three pairs of star-shaped members of FIG. 6 and affixed thereto to form an integral assembly.

FIG. 17 shows a tubular structure of a knitted, woven, or extruded synthetic material to which is sutured a chain of stents.

FIG. 18 shows a structure similar to FIG. 17 but formed in a shape for use in a bifurcated artery.

FIG. 21 shows the patch on the inside of the conduit after it is turned outside-in.

SPECIFIC DESCRIPTION OF THE PREFERRED EMBODIMENT

Figure 1:
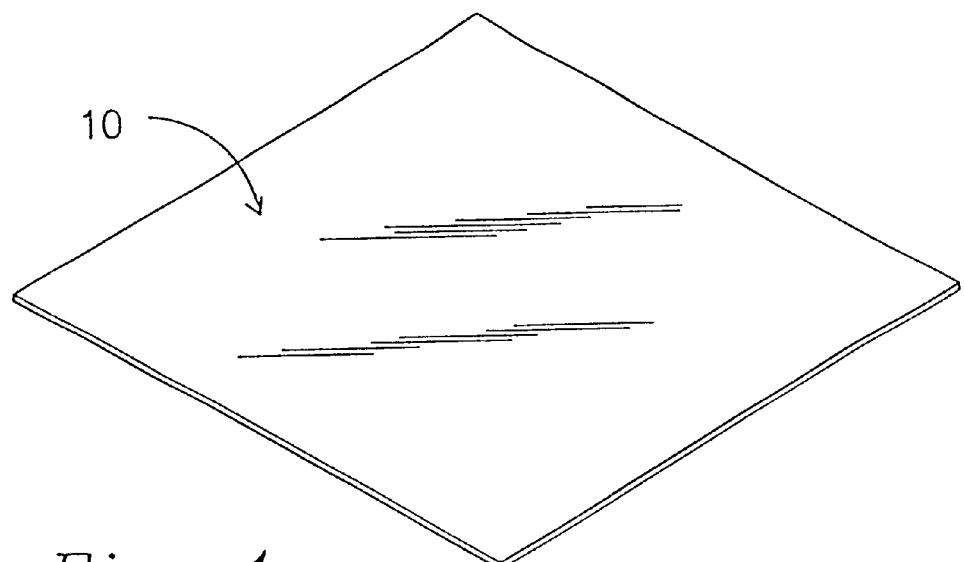
FIG. 1 shows a perspective view of a thin metal sheet from which a star-shaped member may be cut.
Figure 2:
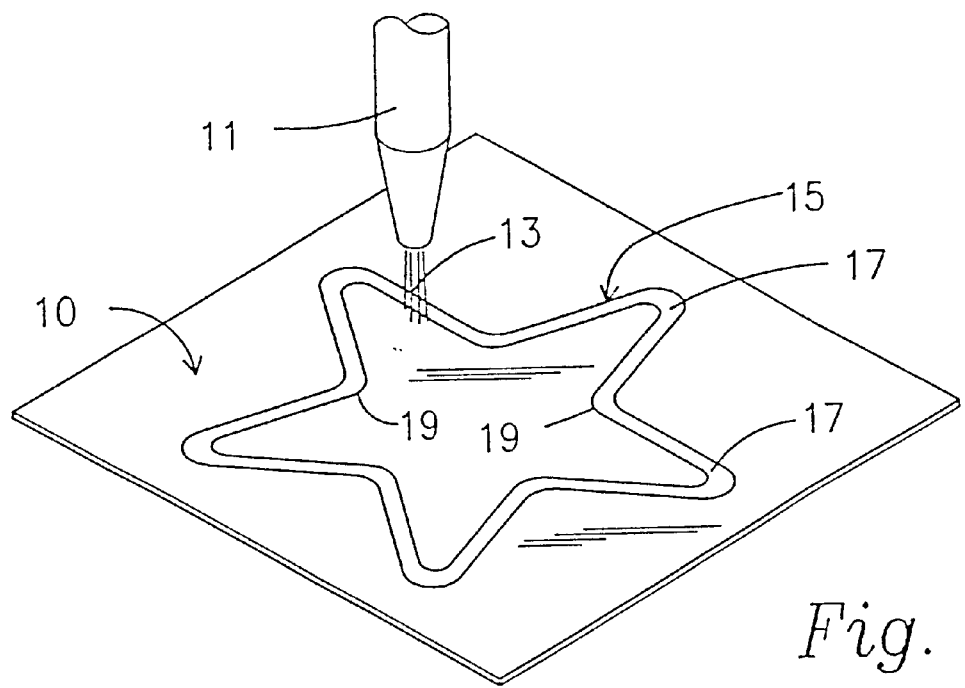
FIG. 2 shows a perspective view of the use of a laser saw to cut a star-shaped member from the metal sheet of FIG. 1.
Figure 7:
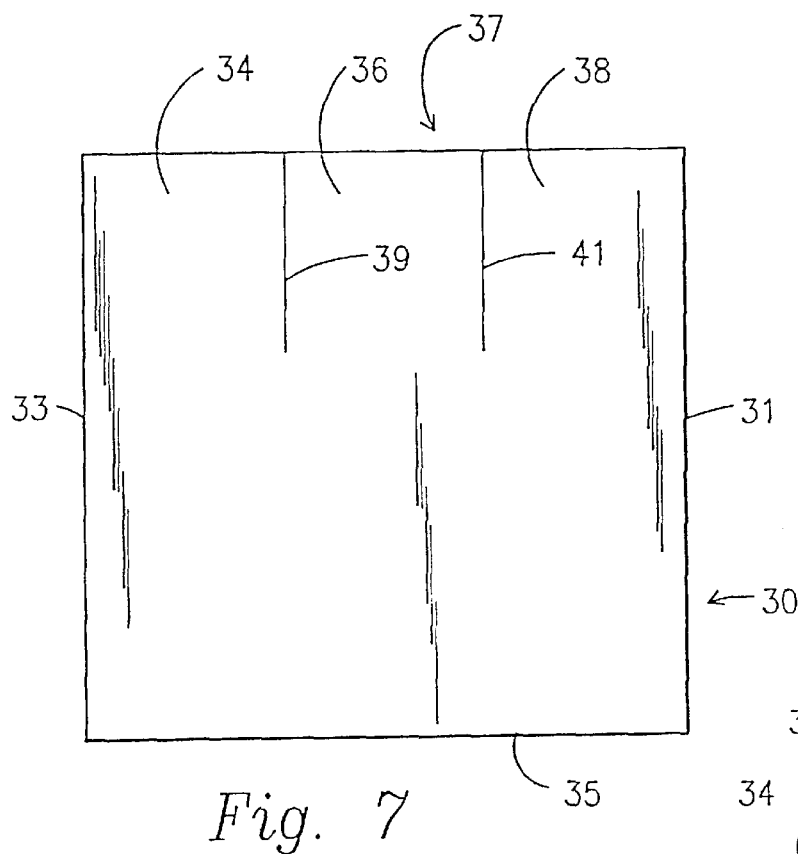
FIG. 7 shows a sheet of flexible bio-compatible material having two slits therein and which will be employed to create a replacement aortic valve tri-cuspid.

With reference, first, to FIG. 1, a metal sheet is generally designated by the reference numeral 10 and is of a uniform thickness, preferably in the range of 25 to 50 mils. With reference to FIG. 2, a laser saw 11 emits a beam 13 that may be used to cut a star-shaped member 15 from the sheet 10. Other processes for cutting out a star-shaped member 15 includes chemical etching, electrolysis and other selective removal techniques. As seen in FIG. 2, the star-shaped member 15 includes five outwardly directed points 17 and five inwardly directed points 19. The center of the star-shaped member 15 is open as best seen with reference to FIG. 3.

With reference to FIG. 4, given the thinness of the metallic material used to create the star-shaped member 15, it may easily be flexed to assume the configuration shown in FIG. 4 with the outwardly directed points 17 sloping downwardly with respect to a plane defined by the inwardly directed points 19.

With reference to FIG. 5, two such star-shaped members, modified as shown in FIG. 4 may be interconnected together by engaging their respective outwardly directed points 17 and welding them together using any suitable technique. As shown in FIG. 5, each star-shaped member 15 has its inwardly directed points 19 free and unattached.

With reference to FIG. 6, a plurality of pairs of star-shaped members 15 such as the pair illustrated in FIG. 5 may be interconnected together by interconnecting pairs of inwardly directed points 19 through any suitable means such as welding to form the structure 20 illustrated in FIG. 6 and consisting of three such pairs of star-shaped members 15 interconnected together. The star shaped members 15 are connected to identical or dissimilar shaped members 15 to form a continuous stent. The welding connections are microwelds created by micro arc welding techniques using a laser welding gun, plasma welding or other welding mechanism well known in the prior art. Since opposed legs of the star-shaped member 15 are welded together, they can be spaced apart to permit introduction of the material used in the weld such as gold or tantalum. Other materials known to accelerate the welding process and improve the strength between the welded elements can be added.

The pattern of welding is important. Not all ends 17 of the star-shaped member 15 are welded together. Rather the welds are restricted to one to three points chosen after the flexibility of the structure 20 is determined.

Figure 8:
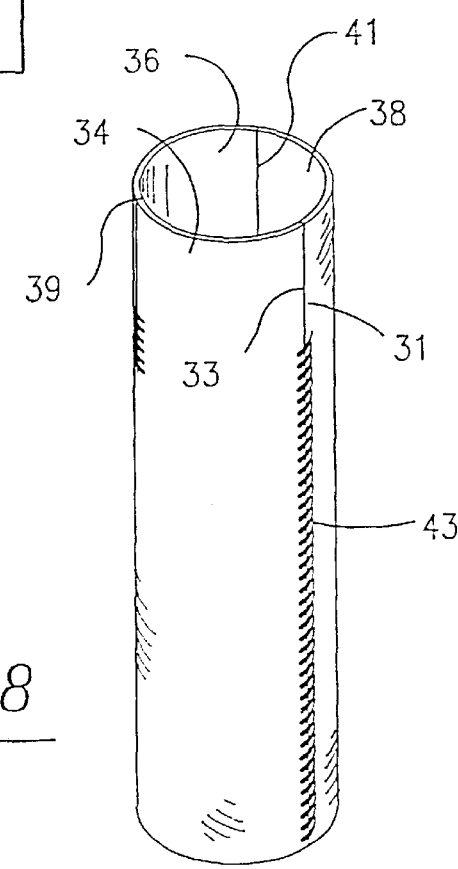
FIG. 8 shows the sheet of FIG. 7 with the open edges thereof sewn together to form a tube.

With reference to FIGS. 7–10, a sheet 30 of a flexible bio-compatible material such as, for example, silk, DACRON, NYLON, polytetrafluoroethylene or polyurethane is formed in a rectangular shape including sides 31, 33, a bottom wall 35, and a top wall 37 in which two slits 39 and 41 are formed to define three flaps 34, 36 and 38. With reference to FIG. 8, the sides 31 and 33 are abutted together and are attached through a technique such as, for example, sewing, employing the thread 43 as shown. Thereafter, with reference to FIG. 9, the three flaps 34, 36 and 38 formed by the slits 39 and 41 are folded in overlapping fashion as seen in FIG. 9 to form a replacement aortic valve tri-cuspid device 45. With reference to FIG. 10, the device 45 may be inserted within the three pairs of star-shaped members 15 assembled together as illustrated in FIG. 6 and described hereinabove and may be affixed therein through sewing at 47 that attaches the members 15 at the area of the inwardly directed points 19 as shown. The device so assembled is designated in FIG. 10 by the reference numeral 50.

Figures 14, 15:
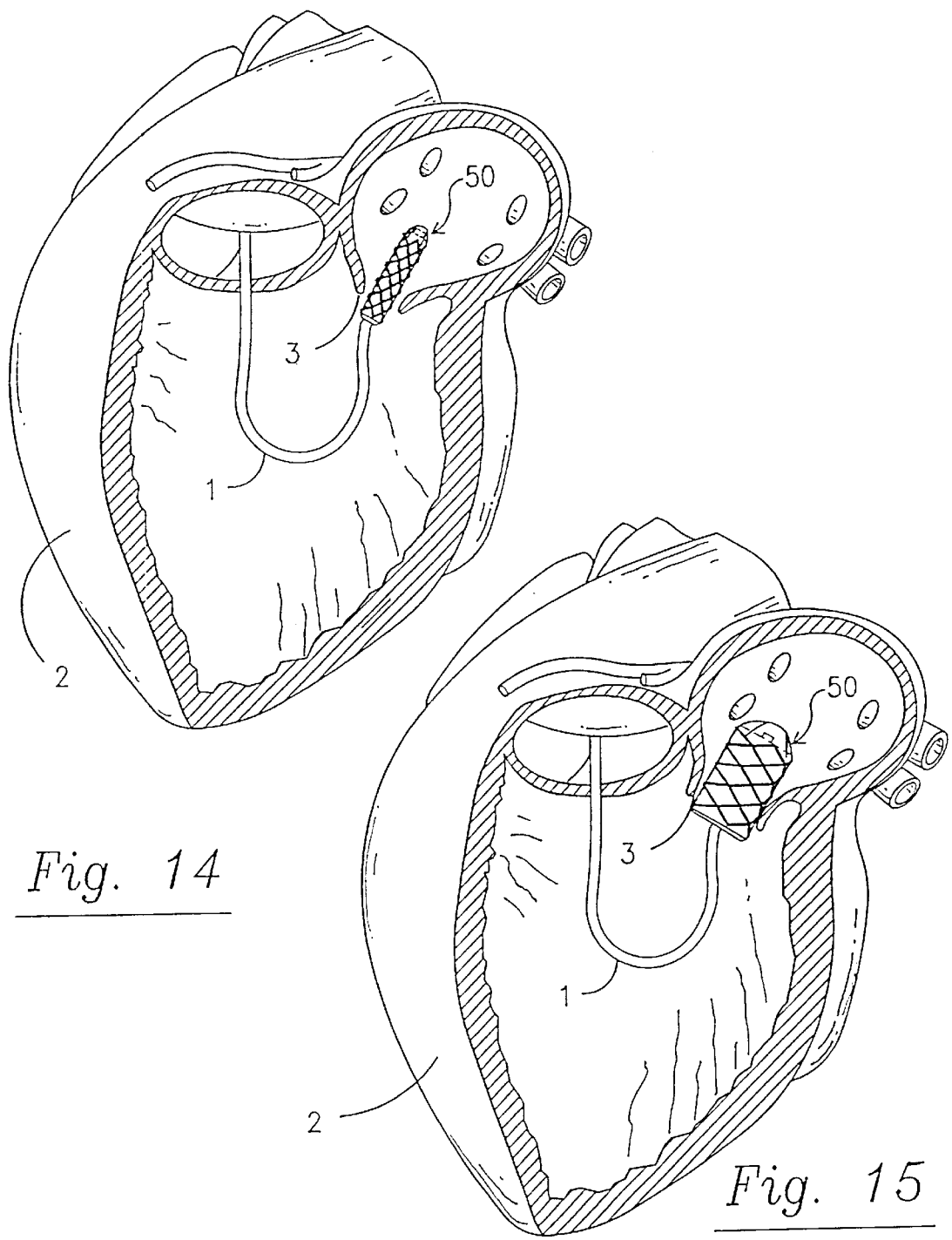
FIG. 14 shows the assembly of FIG. 10 as inserted, through the use of a catheter, within an aortic opening of a heart.
FIG. 15 shows the assembly of FIG. 14 but with the device of FIG. 9 inflated through the use of the catheter so that the entire assembly expands to fill the aortic opening shown.
Figure 16:
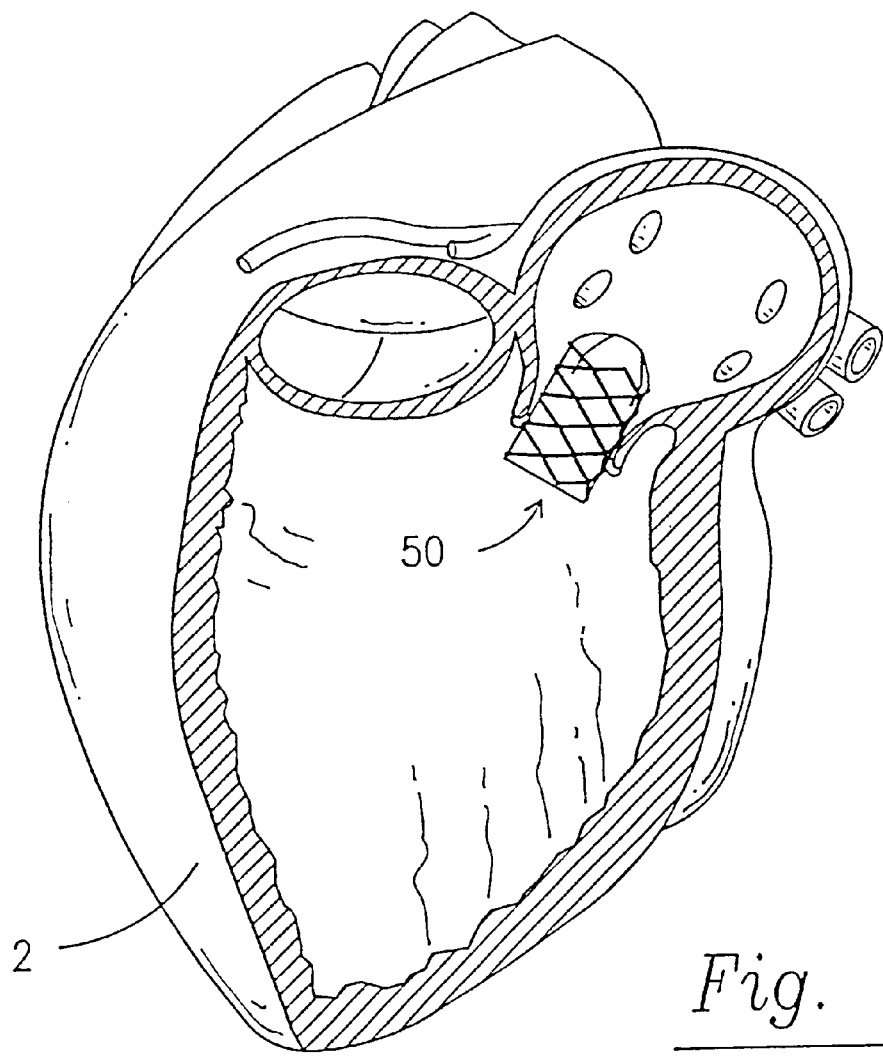
FIG. 16 shows the assembly of FIG. 15 remaining in place after the catheter has been removed therefrom.
Figure 19:
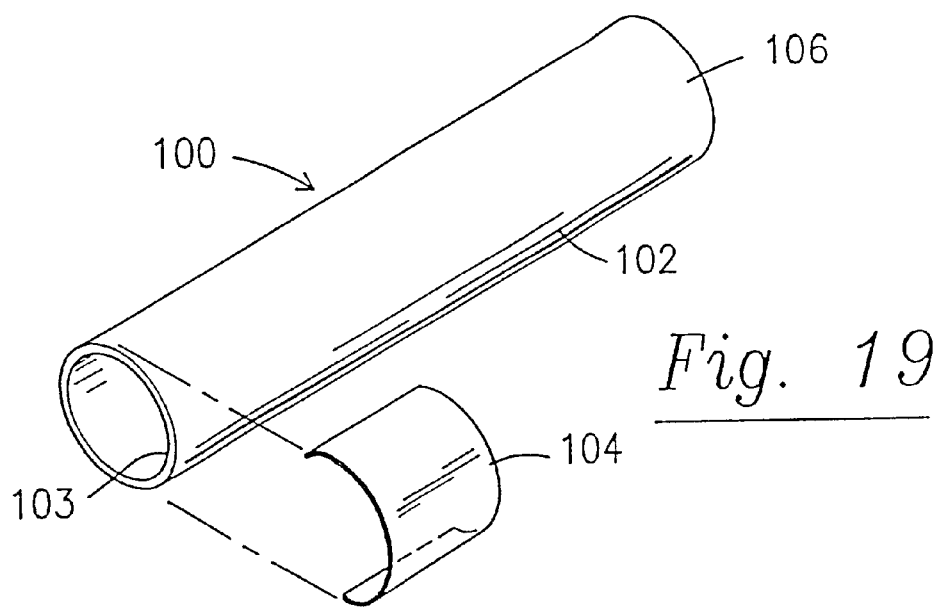
FIG. 19 shows a bio-compatible conduit about to receive a patch made from a like bio-compatible material.

With reference to FIGS. 14, 15 and 16, the device 50 is attached to a catheter 1 and is inserted into an opening 3 in the aortic valve area within the heart 2. As shown in FIG. 15, the catheter 1 is employed to inflate the device 50 so that it fills the opening 3. During this inflation process, the individual star-shaped members 15 are further deformed from their orientation as seen in FIG. 10 and this deformation is maintained once the catheter 1 is removed as shown in FIG. 16 to maintain the device 45 in the expanded state shown to obscure the opening 3 and provide a replacement aortic tri-cuspid valve.

Figure 11:
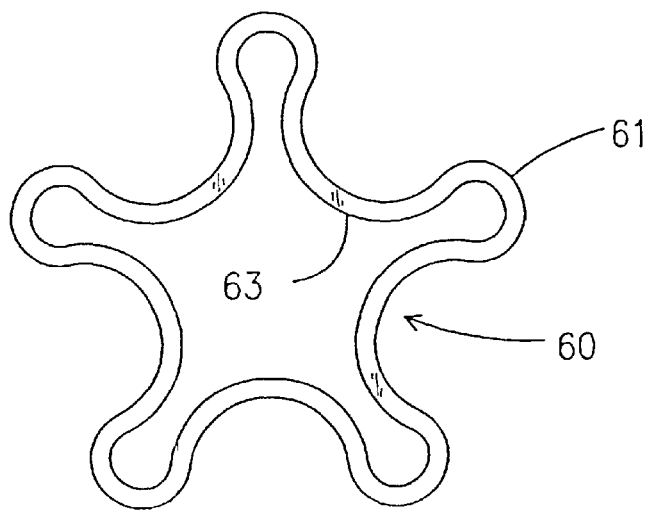
FIGS. 11, 12 and 13 show alternative constructions for the star-shaped members.
Figure 12:
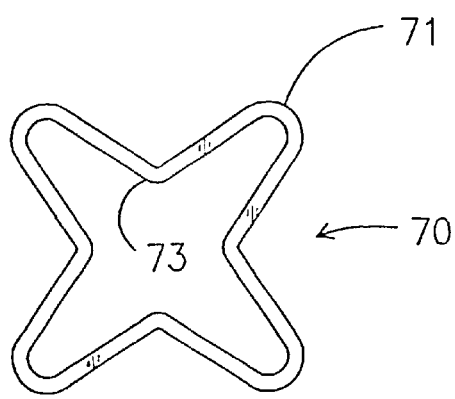
Figure 13:
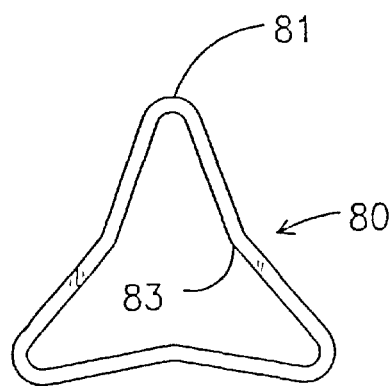

FIGS. 11, 12 and 13 show alternative constructions for the star-shaped member. Thus, FIG. 11 shows a star-shaped member 60 that consists of five arcuately shaped outwardly directed points 61 and five arcuate inwardly directed portions 63. FIG. 12 shows a four pointed star-shaped member 70 having four arcuately shaped outwardly directed points 71 and four inwardly directed points 73. FIG. 13 shows a three pointed star-shaped member 80 having three outwardly directed points 81 and three inwardly directed points 83.

Each of the members 60, 70 or 80 may be employed in the same manner described hereinabove as is the case with the star-shaped member 15. Each of the members 60, 70 or 80 may be formed from a metal sheet such as the metal sheet illustrated in FIG. 1 and employing the same process illustrated in FIG. 2. Each of these members 60, 70 or 80 may be manipulated in the manner described in FIGS. 4, 5 and 6.

In FIGS. 17 and 18 a tube 90 made from knitted, woven or an extruded bio-compatible polymer has a chain of stents 15 sutured 92 to the tube 90. This single graft 94 or the bifurcated graft 96 resulting from the joining of the tube 90 and the stents 15 can be used to replace a diseased portion of an artery in various locations including the heart.

Figure 20:
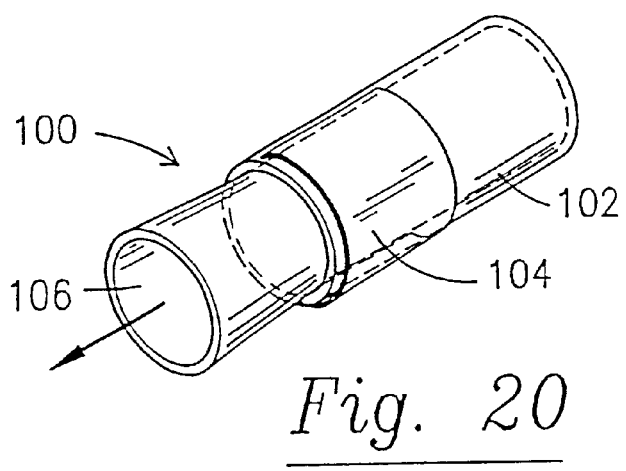
FIG. 20 shows the patch sutured to the outside of the conduit.
Figure 21:
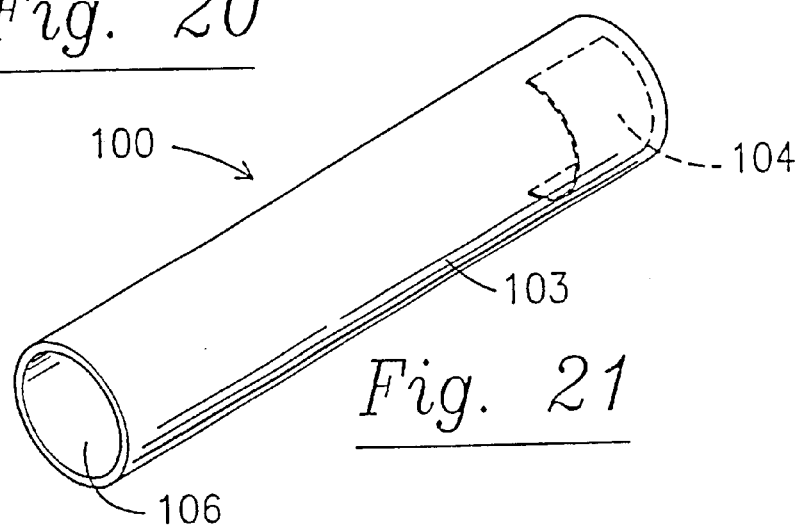
Figure 22:
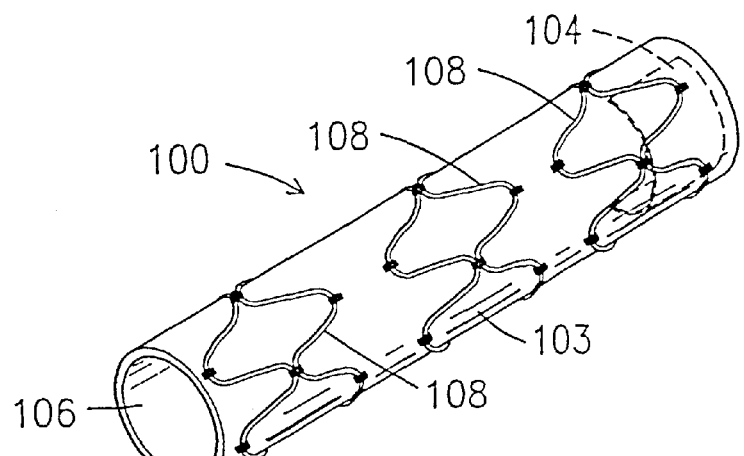
FIG. 22 shows the conduit of FIG. 21 with a stent sutured to the exterior surface.
Figure 23:
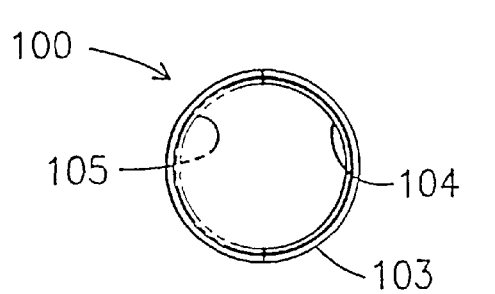
FIG. 23 shows an end view of the conduit of FIG. 21.

An alternate process for preparing a stent graft according to this invention shown in FIGS. 19–25, employs a conduit 100 made from a bovine or synthetic bio-compatible material such as polytetrafluoroethylene, DACRON® or a polyester coated with an anticoagulant such as warfarin or heparin. A single patch 104 is sutured to the exterior 102 of conduit 100. Thereafter, end 106 is pulled inside the conduit 100 as shown in FIG. 20 so that the patch 104 ends up on the inside of the conduit 100 as shown in phantom in FIG. 21. A stent 108 as described in the specification previously as stent 15 is thereafter sutured to the exterior 103 of conduit 100. The single patch 104 acts as a valve as seen in FIG. 23. The blockage of blood flow is shown in phantom with the patch 104 identified as 105 when it acts to block blood flow through the conduit 100.

Figure 24:
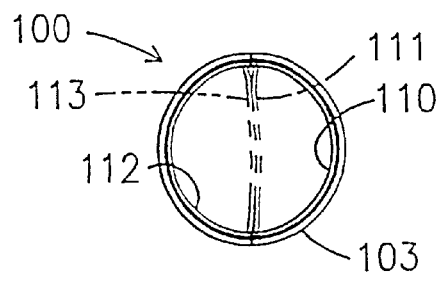
FIG. 24 shows an end view of a conduit with two patches.

Patches 110 and 112 can be sutured to conduit 100 in like manner to patch 104 to form a bicuspid valve as shown in FIG. 24. When patches 110 and 112 are closed (identified now as 111 and 113, respectively) they block flow of blood through conduit 100.

Figure 25:
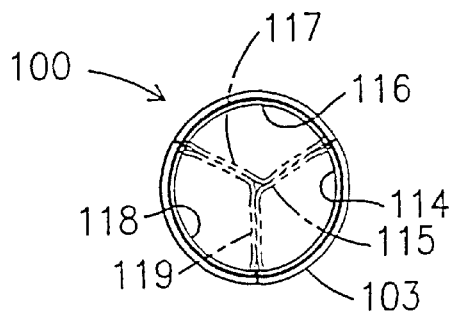
FIG. 25 shows an end view of a conduit with three patches.

Patches 114, 116 and 118 can be sutured to conduit 100 in like manner to patch 104 to form a tri-cuspid valve as shown in FIG. 25. When patches 114, 116 and 118 are closed (identified now as 115, 117, and 119, respectively) they block flow of blood through conduit 100.

Referring again to FIG. 6 the intermediate junction between each star-shaped member 15 can be an octagonal shaped member or other shaped member. Such member has the length of its legs smaller than the star-shaped member 15. This creates a larger segment followed by a smaller segment.

Figure 28:
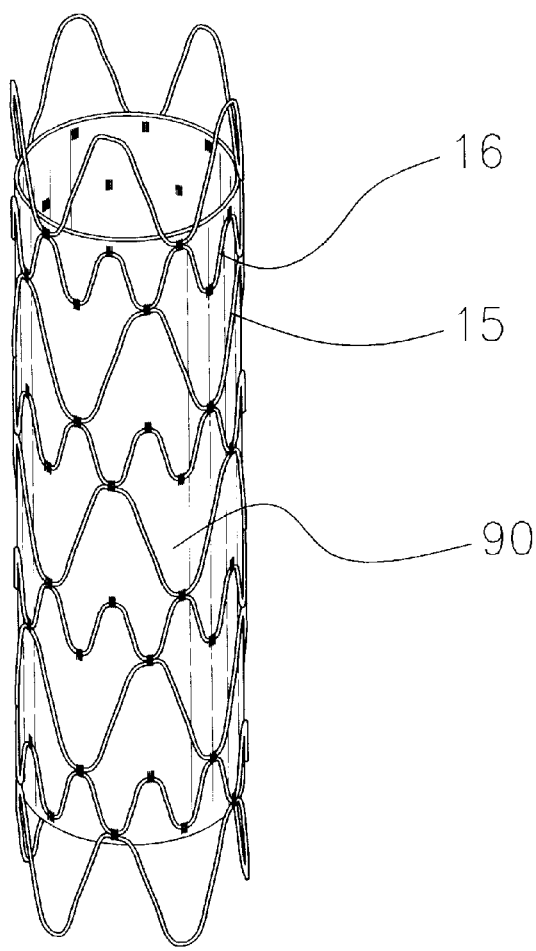
FIG. 28 is an elevational view of a stent overlapping the ends of a graft.
Figure 29:
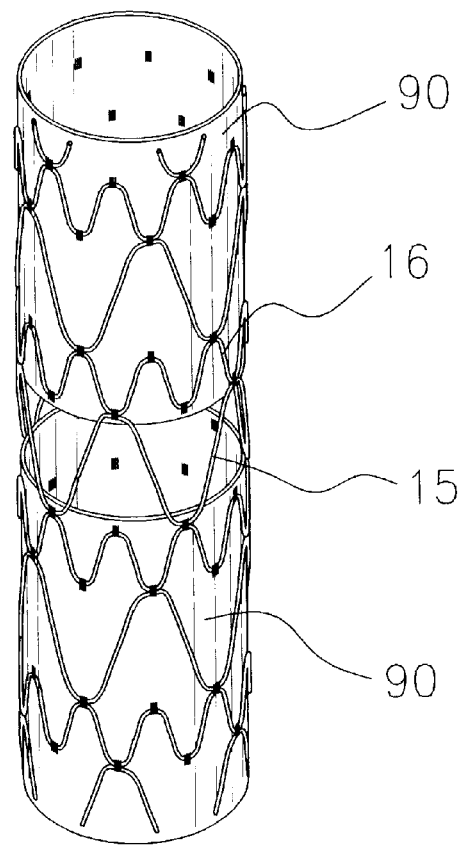
FIG. 29 is an elevational view of a stent having a graft on each end but not in a middle portion.
Figure 30:
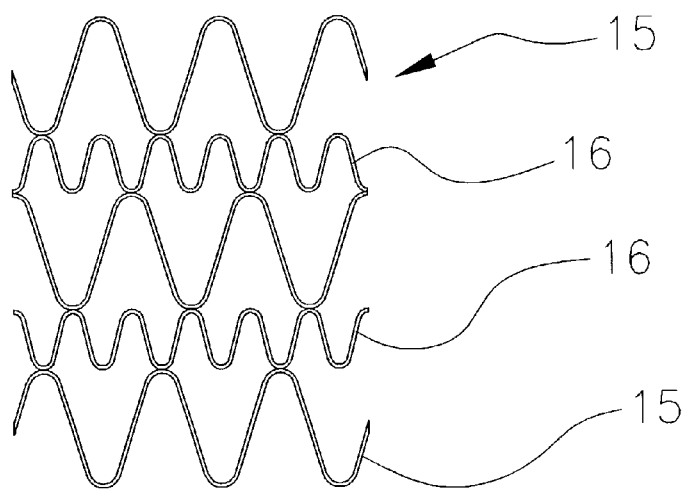
FIG. 30 is a stent with links between the members.

Links 16 can be introduced between star-shaped member 15 to link each member together as illustrated in FIGS. 28 to 30. The links 16 can be straight lines, curved elements, of the same or different materials and can or cannot expand in length upon expansion of the resulting shaped members.

Figure 38:
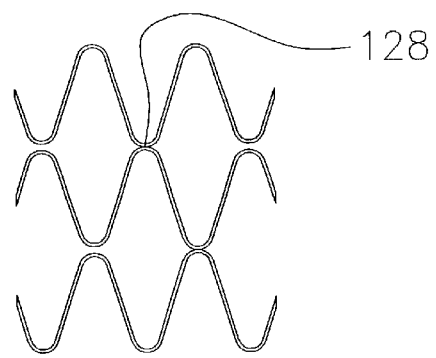
FIG. 38 is a side elevational view of a stent linkage with a weld at one point in each junction.
Figure 39:
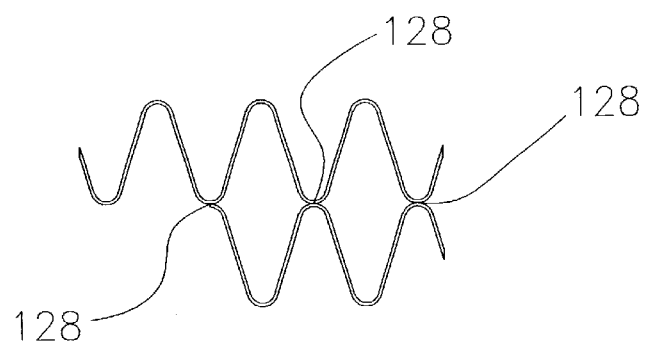
FIG. 39 is a side elevational view of a first alternate stent linkage.
Figure 40:
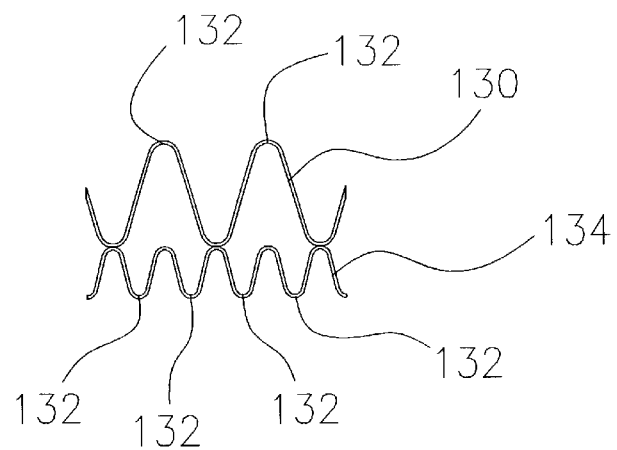
FIG. 40 is a side elevational view of a second alternate stent linkage with a weld at one point on each junction.

Alternate shaped of stents shown in FIGS. 32–37 are identified as 120, 122, 124 and 126. The stents employed in this invention can be welded 128 at one point as shown in FIG. 38 or at multiple points 128 as shown in FIG. 39. A second segment 130 can have half the number of members 132 as a first segment 134.

Figure 41:
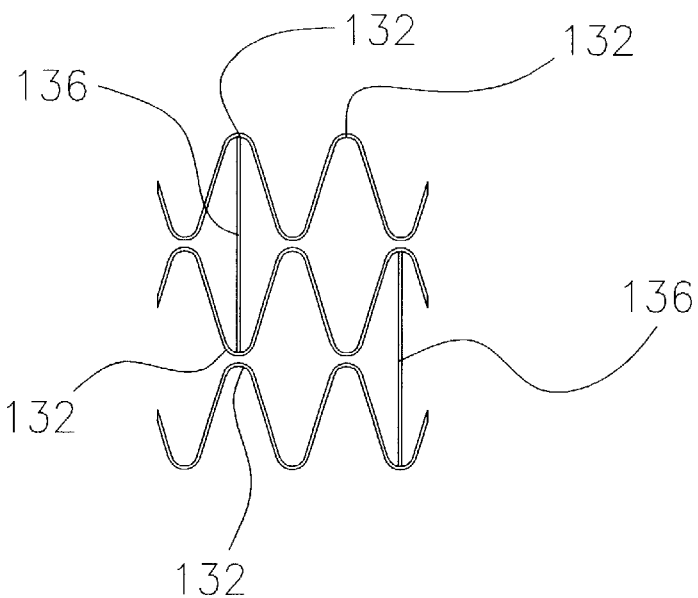
FIG. 41 is a side elevational view of a third alternate stent linkage connected by straight junctions.
Figure 42:
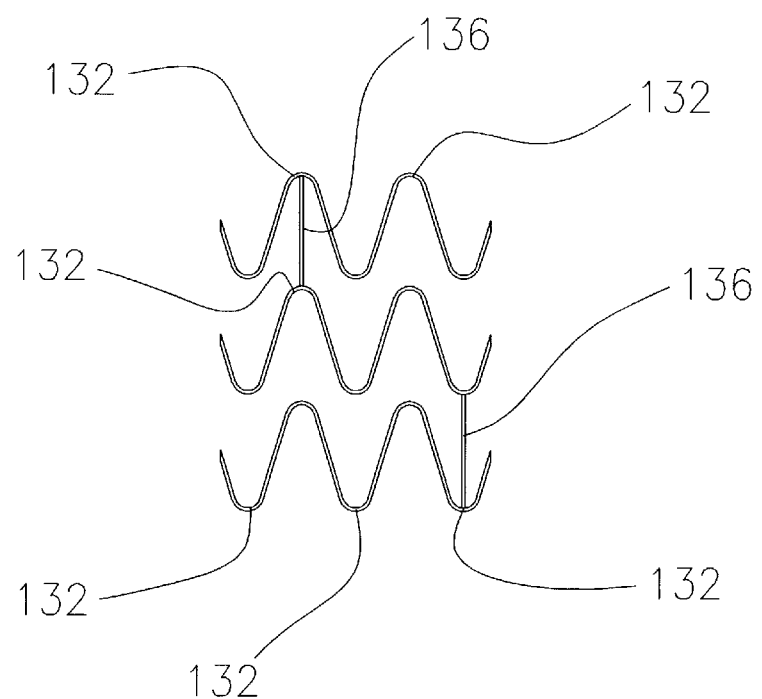
FIG. 42 is a side elevational view of a fourth alternate stent linkage connected by straight junctions.
Figure 43:
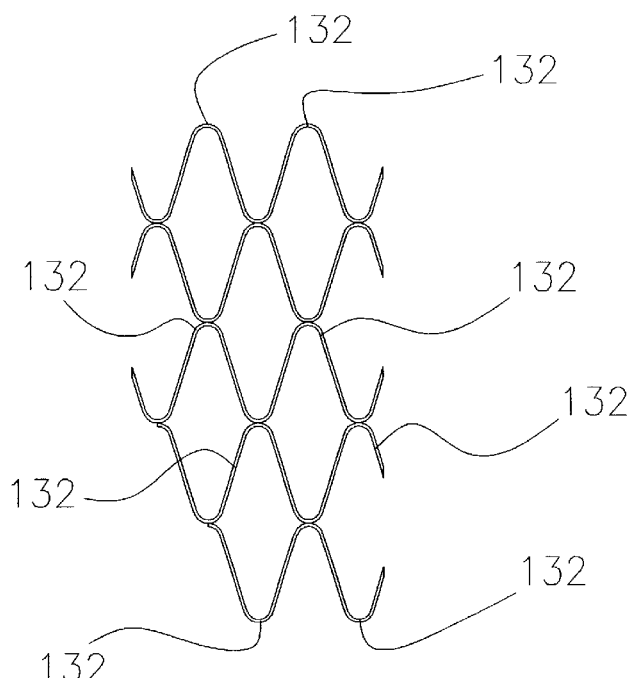
FIG. 43 is a side elevational view of a fifth alternate stent linkage to taper the stent with a combination of members.

Stent members as shown in FIGS. 41 and 42 can be connected by straight junctions 136. Other stents as shown in FIG. 43 can be tapered by using a combination of members 132.

Figure 44:
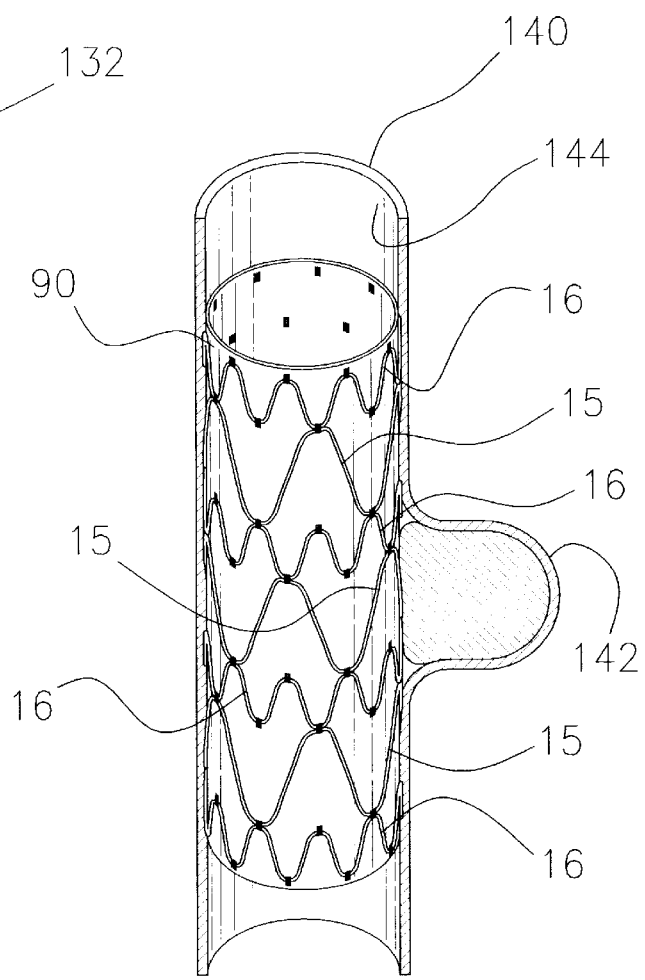
FIG. 44 is a side elevational view of an aortic aneurysm with a stent graft excluding the aneurysm from a vessel wall.
Figures 45, 46:
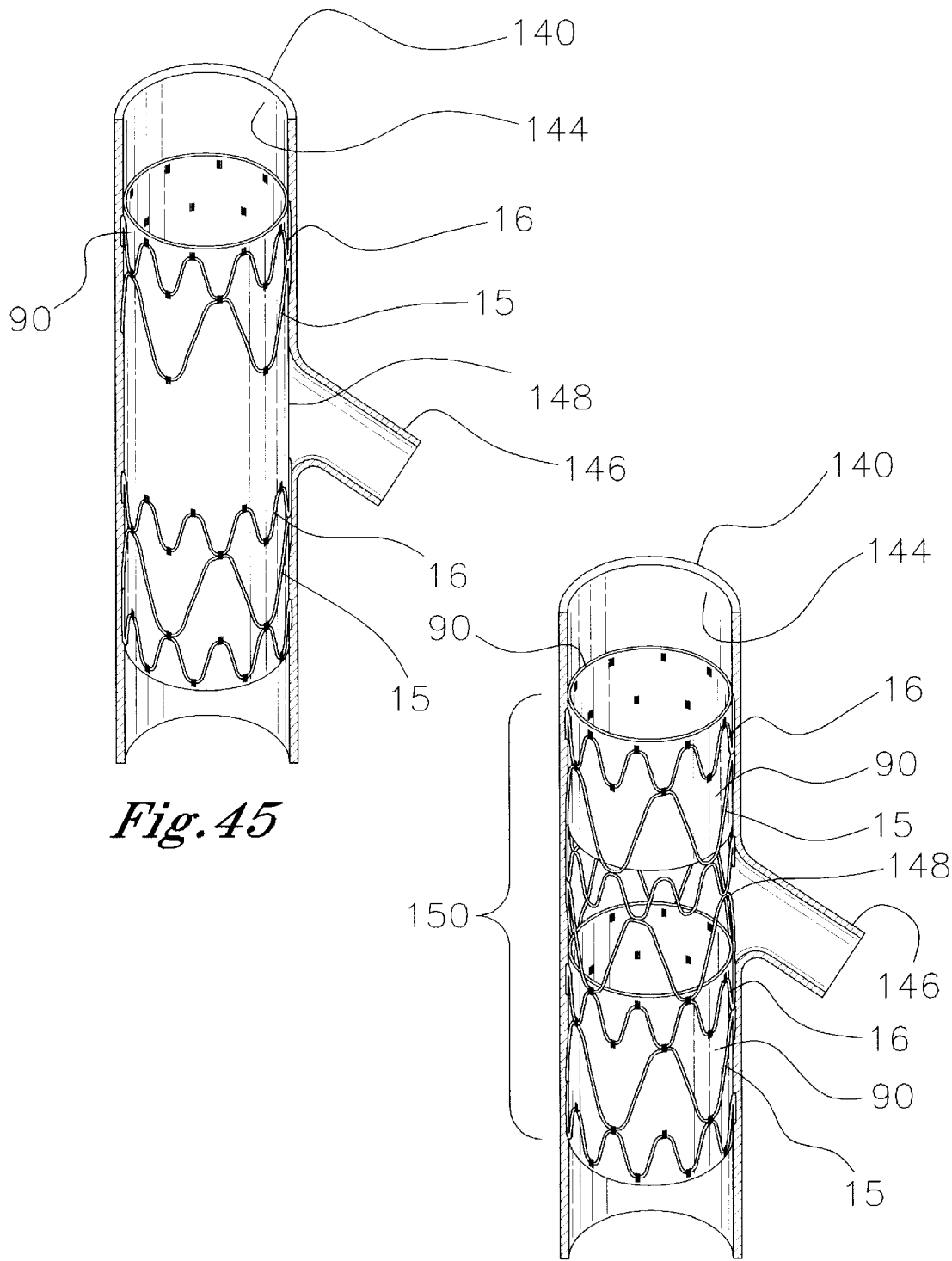
FIG. 45 is a side elevational view of an artery and a side branch artery with a stent in place, but with no stent at the connecting site of the branch artery.
FIG. 46 is a side elevational view of an interconnected stent at a branch artery.

The stent 15, links 16 and tube of biomaterial 90 shown in FIG. 44 is placed in an artery 140 having an aneurysm 142 so that the stent 15, links 16 and biomaterial 90 exclude the aneurysm 142 from the wall 144 of artery 140. In FIG. 45, a side branch 146 of an artery 140 has no stent 15 in the midsection 148. In FIG. 46, the entire stent section 150 is interconnected but the biomaterial 90 is not found in midsection 148 so that blood flow is not impeded to artery branch 146.

The length of the legs of the star-shaped members is also important. These can be of varying lengths. For usage in the small arteries like the coronaries, it is desirable that these lengths be extremely short, in the order of 2 mm or less. The octagonal shaped members which are also used to connect the two star-shaped members can also be less than 2 mm. For larger sized arteries, these lengths can vary. They can be up to 4 mm or sometimes up to 6 mm in length. Hence when ten of the 4 mm long star-shaped members are joined together, then we have a 40 mm long stent. The flat sheet from which these members can be made, are of NITINOL, titanium-nickel alloy, stainless steel or tantalum.

The star-shaped member 15 can also be assembled together such that the alternate members are made from different materials. The first member could be stainless steel, while the second member could be made from NITINOL and could alternate along the length of the stent. In a case like this the stent becomes partially balloon expandable and partially self expandable. Hence the stent does not expand due to elastic deformation completely but only partially due to the elastic deformation of the stainless steel and partially due to self expanding properties of the NITINOL. The NITINOL also can have shape memory characteristics.

If a combination of two different materials are used, then the wall thickness of the two materials which form the two members can differ. It is not necessary that we need to form the entire length of the stent with a single wall or strut thickness. Similarly the length of the legs of the star-shaped members may also differ. For example, the member 15 made of stainless steel may have a length of 2 mm, while the alternate member made of a material like NITINOL can have a length of 3 mm and vice versa.

In the same member 15 the length of the various legs can vary. For example, a star-shaped member 15 has five legs. Instead of all five legs having a length of 2 mm, it is possible that the length of four of the legs are each 2 mm and the other leg is 3 mm. Two of the legs could be 3 mm, while the other three could be 2 mm.

When a first member 15 is attached at a point on to the second member 15 through a suitable micro-welding arrangement, the second member may or may not be attached at the same line of point to a third member 15. It may be attached at a different point to the third member and this may rotate for the fourth member, fifth member, etc.

Depending on the length and diameter of the stent, one can choose to go either with a star-shaped member or an octagonal shaped member. If one wants a very short length of the stent; ie, 4 mm as is used in some neurovascular application, then it is possible that we use two of the star-shaped members 15 which are 2 mm segments welded together. If we decide to go with only one member that forms the entire length of 4 mm, then we can decide to go with an octagonal member. This gives us the adequate coverage towards the total length of the segment in the artery to be stented.

Figure 26:
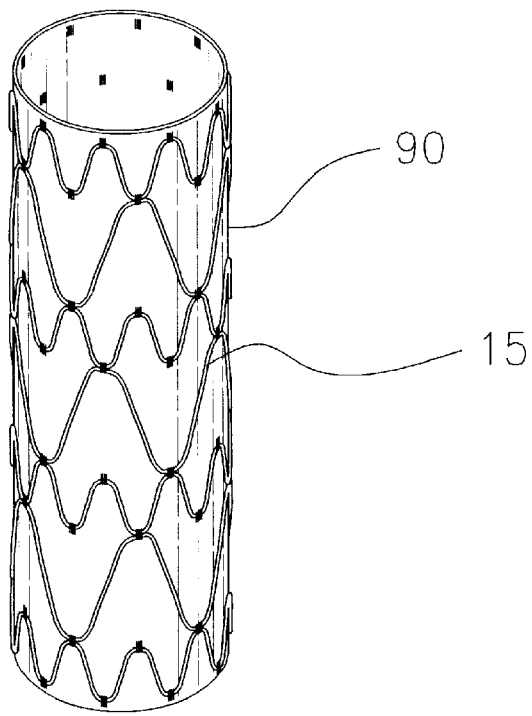
FIG. 26 is an elevational view of a stent covering the outside of a graft.
Figure 27:
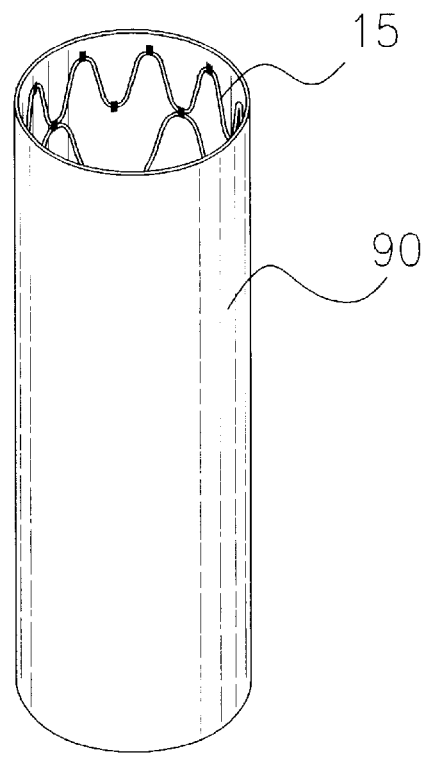
FIG. 27 is an elevational view of a graft with a stent on its inside surface.

In embodiments where the stent is attached to a graft 90 or 96 the following combinations also can be possible. First the stent 15 is formed of the desired diameter and the length and the members are attached to one another. After the total length of the stent is formed, a graft 90 or 96 which is a fabric (polyester) or an extruded tube (PTFE) is taken and then the stent is attached either externally or internally as shown in FIGS. 26 and 27. The total length of the stent and the graft may not exactly match with one another. See FIG. 28. The stent 15 can be 20 mm long, while the graft 90 or 96 only can be 15 mm long. In this case 2.5 mm on either end of the stent 15 is left exposed on both ends of the graft 90 or 96 distally and proximally as seen in FIG. 28. This provides for better anchoring at the site of the implantation.

Growth factors, antirectanoic factors and genetic materials can be incorporated in the body of the stent by itself or through a carrier mechanism.

The 2.5 mm on either side can be a member made of NITINOL which means only the ends of the graft 90 or 96 self expand, while the middle portion of the graft 90 which has stainless steel expands with the help of a balloon. The entire stent also can be of NITINOL. In which case all the members 15 that form the entire length of the stent can be a combination of shape-memory metal and super-elastic metal. The members 15 on the ends which are exposed with no graft 90 on them can be shaped for memory, while the entire length of the stent can be super elastic. The super elastic and the shape memory members can be welded together. In the expanded stage the outer diameter of the stent is substantially the same as the inner diameter of the blood vessel or non-vascular conduit in the human body.

It is also possible that the middle portion of the stent graft has to be placed against a bifurcation or a side branch that cannot be compromised while implanting the stent graft. In such a case the graft is chosen such that it terminates at one point along the length of the stent, but resumes again after an interval. There also may be several termination points and starting points as desired by the anatomy of the body. Another method to obtain the gaps in the stent graft is to strip the fabric or the extruded tube of the polymer and leave the stent studs as they are. This is accomplished by the currently existing wire stripping techniques. See FIG. 29.

For the stent graft applications, the stents may or may not be welded together. The stents may be placed at equal distances of each other on the surface of the graft and then attached to the graft by any suitable attachment mechanisms. These include but is not limited to the suture attachment methods, where a suture going around each strut of the member is attached to the fabric or the extruded tube. Apart from the suturing techniques, methods including adhesives also may be used.

Figure 31:
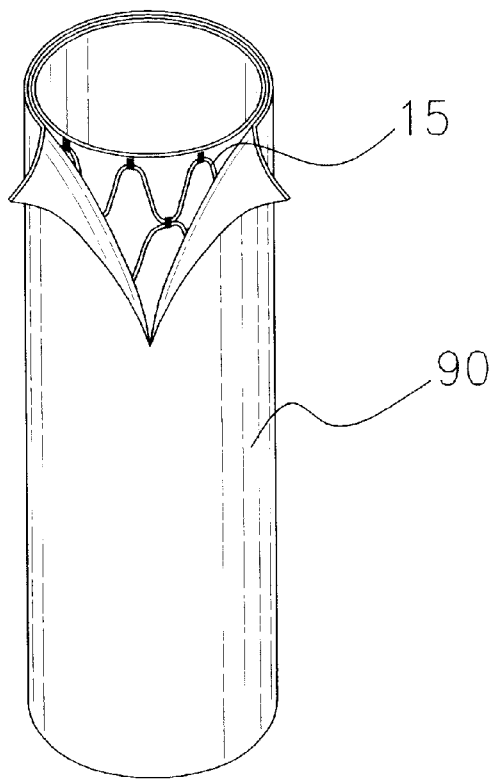
FIG. 31 shows a stent sandwiched between two polymer layers.
Figure 32:
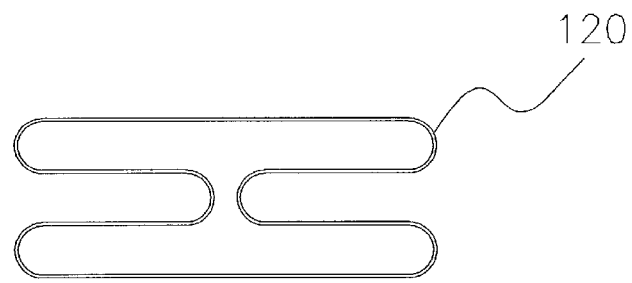
FIG. 32 is a side elevational view of a base design for a stent.
Figure 33:
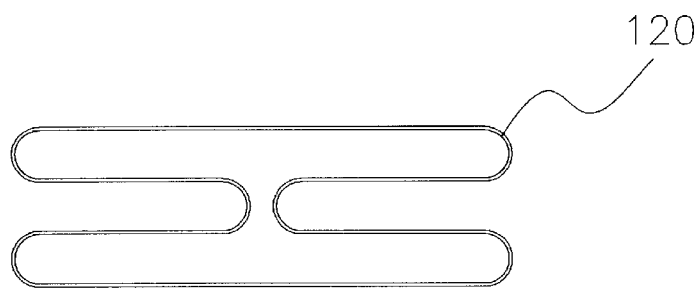
FIG. 33 is an enlarged version of the base stent of FIG. 32.
Figure 34:
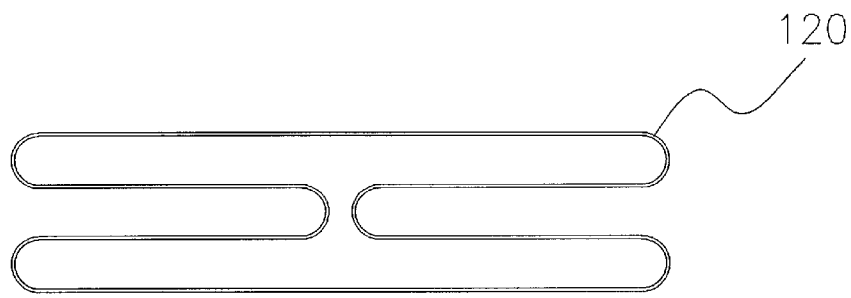
FIG. 34 is an enlarged version of the base stent of FIG. 33.
Figure 35:
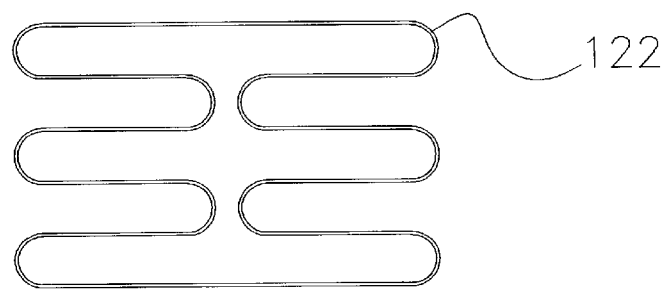
FIG. 35 is a side elevational view of a first alternate base stent design.
Figure 36:
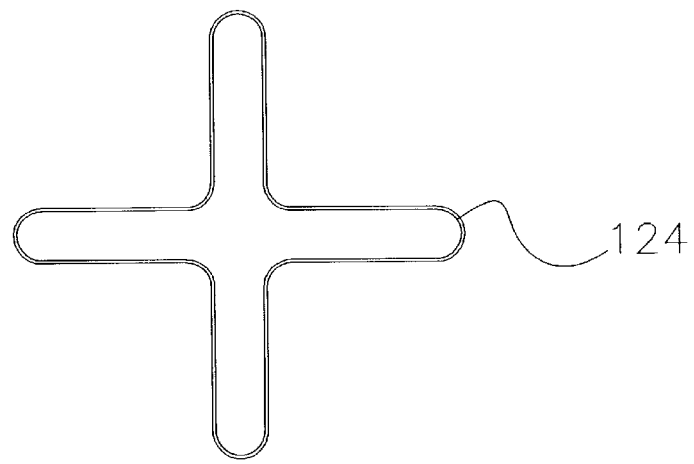
FIG. 36 is a side elevational view of a second alternate base stent design.
Figure 37:
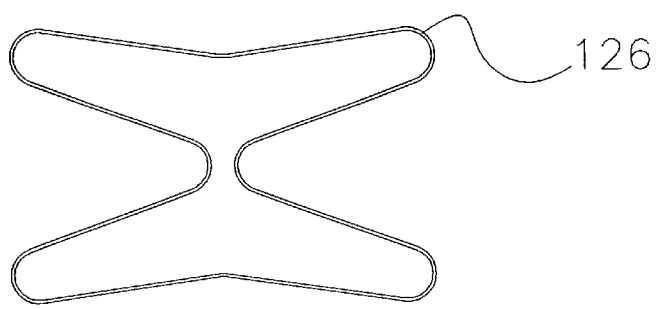
FIG. 37 is a side elevational view of a third alternate base stent design.

One other embodiment is as the tube is being extruded, the stent members may be supplied into the extrusion process such that the stent and the extruded tube are jointly extruded together. The location of the stent on the tube may be either on the outside of the tube, inside of the extruded tube or the middle layer of the extruded tube. When the first inner layer of the tube is extruded, the stent members are supplied into it and then the second or the outer layer is extruded. The stent is completely imbedded inside the two layers as seen in FIG. 31.

When the stent is on the outside, the members 15 are arranged equidistant from each other. They form a pattern on the outside of the extruded tube or the fabric. A star-shaped member or any other suitable shape may be chosen. The shape to be chosen also has to do with the diameter of the extruded tubing.

As such, an invention has been described in terms of a preferred embodiment thereof which fulfills each and every one of the objects of the invention as set forth hereinabove and provides a new and useful star-shaped stent and replacement valve for use in repairing a damaged cardiac valve of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A stent comprising:
   a) a plurality of star-shaped members, each including:
      i) a plurality of outwardly directed points and an equal plurality of inwardly directed points;
      ii) an open center;
      iii) said outwardly directed points being bent and facing away from a plane defined by said inwardly directed points; and
   b) said star-shaped members being connected together by identical or dissimilar shaped members to form a continuous stent.

2. The stent of claim 1, wherein said star-shaped members are connected together by a micro-weld that fastens at least one outwardly directed point of one star-shaped member with a corresponding outwardly directed point of an adjacent star-shaped member.

3. The stent of claim 1, wherein said star-shaped members are connected together by a micro-weld that fastens at least one inwardly directed point of one star-shaped member with a corresponding inwardly directed point of an adjacent star-shaped member.

4. The stent of claim 2, wherein adjacent said star-shaped members form a pair of star-shaped members, and further including two pairs of star-shaped members being fastened together by a micro-weld that fastens at least one inwardly directed point of one star-shaped member of one such pair with a corresponding inwardly directed point of one star-shaped member of an adjacent pair.

5. The stent of claim 3, wherein adjacent said star-shaped members form a pair of star-shaped members, and further including two pairs of star-shaped members being fastened together by a micro-weld that fastens at least one outwardly directed point of one star-shaped member of one such pair with a corresponding outwardly directed point of one star-shaped member of an adjacent pair.

6. The stent of claim 1 placed in a vascular conduit of the human body to relieve a constriction and create an open channel for communication.

7. The stent of claim 1 placed in a non-vascular conduit of the human body to relieve a constriction and create an open channel for communication.

8. The stent of claim 6 mounted on a balloon catheter which expands the stent from a first diameter size to a second diameter size having the same exterior diameter as the inner diameter of the vascular conduit.

9. The stent of claim 7 mounted on a balloon catheter which expands the stent from a first diameter size to a second diameter size having the same exterior diameter as the inner diameter of the non-vascular conduit.

10. A method of making a stent from a flat two-dimensional metal sheet including the steps of:
    a) forming a plurality of flat star-shaped members each including a plurality of outwardly directed points and an equal plurality of inwardly directed points and an open center;
    b) bending said outwardly directed points so that they face away from a plane defined by said inwardly directed points;
    c) fastening said star-shaped members together with an octagonal shaped member.

11. The method of claim 10, wherein said fastening step includes the step of micro-welding said star-shaped members together by fastening at least one outwardly directed point of one star-shaped member with a corresponding outwardly directed point of an adjacent star-shaped member.

12. The method of claim 10, wherein said fastening step includes the step of micro-welding said star-shaped members together by fastening at least one inwardly directed point of one star-shaped member with a corresponding inwardly directed point of an adjacent star-shaped member.

13. The method of claim 11, wherein adjacent said star-shaped members form a pair of star-shaped members, and said method further including the step of fastening two pairs of star-shaped members together by fastening at least one inwardly directed point of one star-shaped member of one such pair with a corresponding inwardly directed point of one star-shaped member of an adjacent pair.

14. The method of claim 12, wherein adjacent said star-shaped members form a pair of star-shaped members, and said method further including the step of fastening two pairs of star-shaped members together by fastening at least one outwardly directed point of one star-shaped member of one such pair with a corresponding outwardly directed point of one star-shaped member of an adjacent pair.

15. The method of claim 10 wherein the plurality of flat-star shaped members are derived from cutting a flat metal sheet of a material selected from the group consisting of stainless steel, titanium, elgiloy or nickel-titanium alloy and joining star-shaped members from different material metal sheets together.

16. A stent comprising:
   a) a plurality of star-shaped members, each including:
      i) a plurality of at least three outwardly directed points and a like number of inwardly directed points;
      ii) an open center;
      iii) said outwardly directed points being bent and facing away from a plane defined by said inwardly directed points;
   b) said star-shaped members being micro-welded together; and
   c) a graft tubular body fastened to said star-shaped members.

17. The stent according to claim 16 wherein the star-shaped members are sutured to the tubular body.

18. The stent according to claim 17 wherein the tubular body is bifurcated.

19. The stent according to claim 16 wherein the tubular body is a knitted, woven or extruded polymeric material acceptable to living tissue.

20. The stent according to claim 16 wherein a material selected from the group consisting of an anti-coagulant, growth factor, antirestonoic factors and genetic material is incorporated on the graft tubular body.

21. The stent according to claim 16 wherein the plurality of star-shaped members are on an outside surface of the graft tubular body.

22. The stent according to claim 16 wherein the graft tubular body surrounds the plurality of star-shaped members.

23. The stent according to claim 16 wherein the plurality of star-shaped members are on an outside surface of two graft tubular bodies and a middle portion of the star-shaped member is separated from the graft tubular body.

24. A stent formed from the stent joined to the graft tubular body of claim 16 employed as a heart valve.

25. A stent formed from the stent joined to the graft tubular body of claim 16 employed to correct an arterial aneurysm.

26. The stent according to claim 20 wherein the material is incorporated into the graft tubular body through a controlled release agent selected from the group consisting of a synthetic biodegradable compound, a non-biodegradable compound, a biologically derived protein and a liposome.

* * * * *